| United States Patent [19] | [11] Patent Number: 4,533,738 |
| --- | --- |
| Takaya et al. | [45] Date of Patent: Aug. 6, 1985 |

[54] NEW CEPHEM COMPOUNDS AND PROCESSES FOR PREPARATION THEREOF

[75] Inventors: Takao Takaya, Kawanishi; Yoshikazu Inoue, Amagasaki; Masayoshi Murata, Mino; Hisashi Takasugi, Kohamanishi, all of Japan

[73] Assignee: Fujisawa Pharmaceutical Co., Ltd., Osaka, Japan

[21] Appl. No.: 523,594

[22] Filed: Aug. 16, 1983

Related U.S. Application Data

[62] Division of Ser. No. 296,860, Aug. 27, 1981, Pat. No. 4,416,879.

[30] Foreign Application Priority Data

Sep. 8, 1980 [GB] United Kingdom ............... 8028933

[51] Int. Cl.$^3$ ........................................... C07D 417/12
[52] U.S. Cl. ...................................................... 548/194
[58] Field of Search ......................................... 548/194

[56] References Cited

U.S. PATENT DOCUMENTS 4,284,631 8/1981 Takaya ............................. 424/246
4,416,879 11/1983 Takaya ............................. 424/246

Primary Examiner—Robert Gerstl
Attorney, Agent, or Firm—Oblon, Fisher, Spivak, McClelland & Maier

[57] ABSTRACT

Thiazole intermediates for cepham compounds are described.

6 Claims, No Drawings

NEW CEPHEM COMPOUNDS AND PROCESSES FOR PREPARATION THEREOF

This is a division of application Ser. No. 296,860, filed Aug. 27, 1981, now U.S. Pat. No. 4,416,879.

The present invention relates to new cephem compounds and pharmaceutically acceptable salts thereof. More particularly, it relates to new cephem compounds and pharmaceutically acceptable salts thereof, which have antimicrobial activities and to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I).

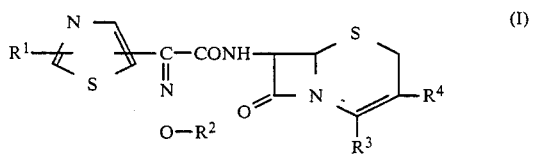

wherein $R^1$ is amino or a protected amino group;
$R^2$ is a saturated 4 to 8-membered heteromonocyclic group containing one sulfur atom;
$R^3$ is carboxy or a protected carboxy group; and
$R^4$ is hydrogen, lower alkyl, or a group of the formula:

—$CH_2R^{4a}$ (wherein $R^{4a}$ is acyloxy, a heterocyclicthio group which may have suitable substituent(s) or pyridinio which may have suitable substituent(s)], with proviso that $R^3$ is $COO^-$ when $R^{4a}$ is pyridinio which may have suitable substituent(s).

According to the present invention, the new cephem compounds (I) can be prepared by various processes which are illustrated in the following schemes.

PROCESS 1

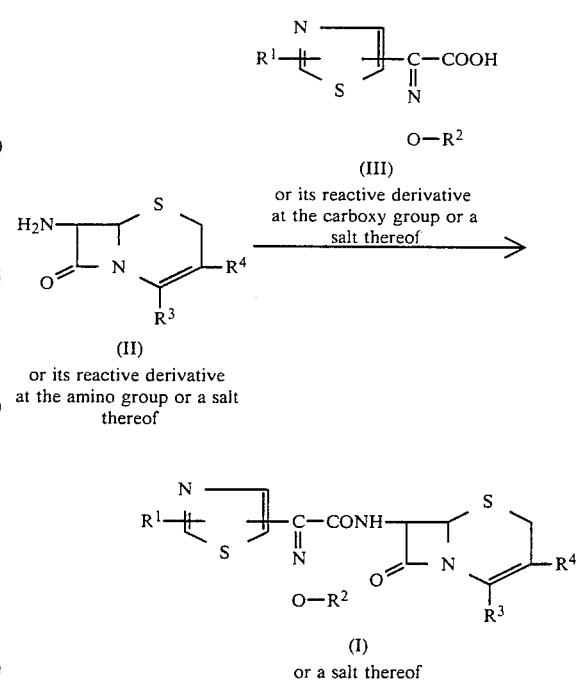

PROCESS 2

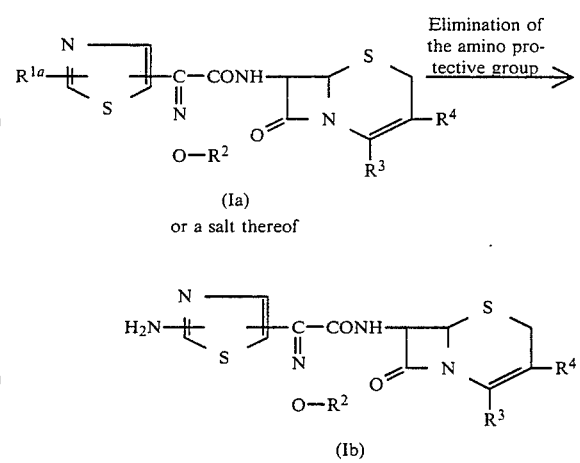

PROCESS 3

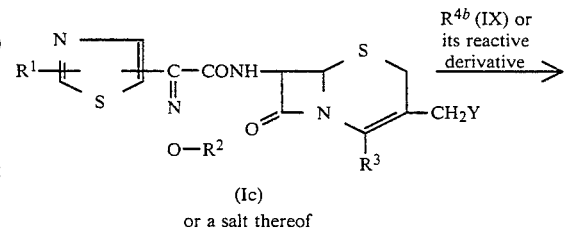

-continued

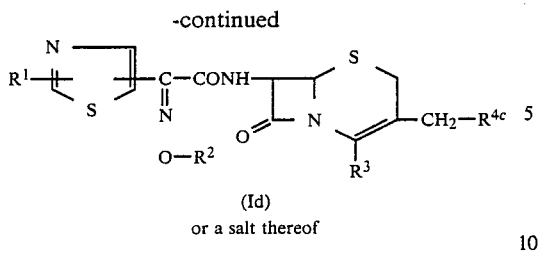

(Id)
or a salt thereof wherein $R^1$, $R^2$, $R^3$ and $R^4$ are each as defined above;
$R^{1a}$ is a protected amino group;
$R^{4b}$ is a heterocyclicthiol which may have suitable substituent(s) or pyridine which may have suitable substituent(s);
Y is a group which can be substituted by a group of the formula: $-R^{4c}$ in which $R^{4c}$ is a heterocyclicthio group which may have suitable substituent(s) or pyridinio which may have suitable substituent(s); and
$R^{4c}$ is as defined above.

Among the starting compounds in the present invention, the compound (III) is novel and can be prepared by the processes which are illustrated in the following schemes.

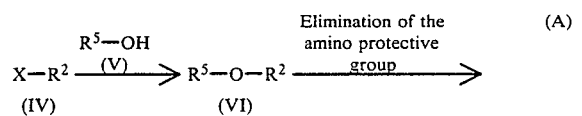

(A)

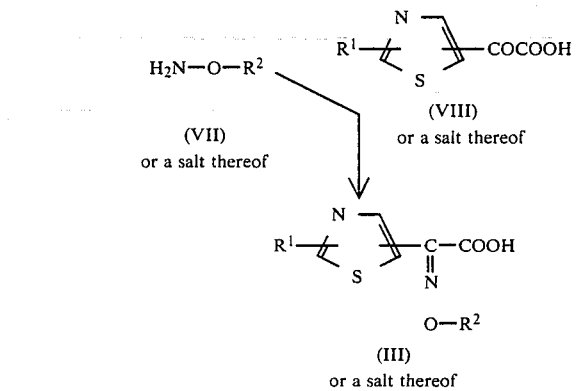

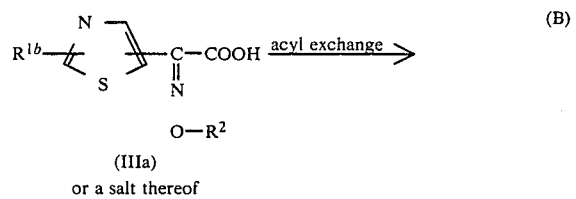

(B)

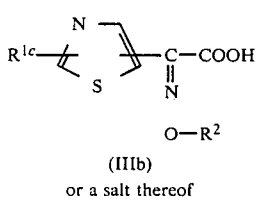

wherein $R^1$ and $R^2$ are each as defined above,
X is hydroxy or its reactive derivative,
$R^5$ is amino having a protective group,
$R^{1b}$ is lower alkanoylamino, and
$R^{1c}$ is trihalo(lower)alkanoylamino.

Regarding the object compounds [I], [Ia], [Ib], [Ic] and [Id] and the starting compounds (III), (IIIa), (IIIb) and (VIII), it is to be understood that they include tautomeric isomers. That is, in case that the group of the formula:

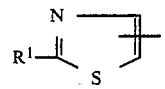

($R^1$ is as defined above) is contained in the molecules of said object and starting compounds, said group of the formula can also be alternatively represented by its tautomeric formula:

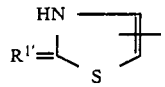

($R^{1'}$ is imino or a protected imino group.) That is, the both of said groups are in the state of equilibrium each other and such tautomerism can be represented by the following equilibrium.

wherein $R^1$ and $R^{1'}$ are each as defined above.

These types of tautomerism between the amino-compound and the corresponding imino-compound as stated above have been well known in the literature, and it is obvious to a person skilled in the arts that both of the tautomeric isomers are easily convertible reciprocally and are included within the same category of the compound per se. Accordingly, the both of the tautomeric forms of the object compounds [I], [Ia], [Ib], [Ic] and [Id] and the starting compounds (III), (IIIa), (IIIb) and (VIII) are clearly included within the scope of the present invention. In the present specification and claims, the object and starting compounds including the group of such tautomeric isomers are represented by using one of the expressions therefor, that is the formula:

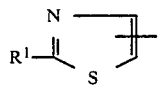

Furthermore, regarding the object compounds [I], [Ia], [Ib], [Ic], and [Id] and the starting compounds [III], [IIIa] and [IIIb], it is to be understood that said object and starting compounds include syn isomer, anti isomer and a mixture thereof. For example, with regard to the object compound (I), syn isomer means one geometrical isomer having the partial structure represented by the following formula:

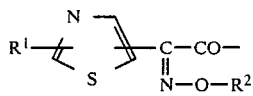

(wherein R¹ and R² are each as defined above) and anti isomer means the other geometrical isomer having the partial structure represented by the following formula:

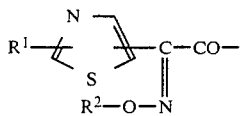

(wherein R¹ and R² are each as defined above).

Regarding the other object and starting compounds as mentioned above, the syn isomer and the anti isomer can also be referred to the same geometrical isomers as illustrated for the compound (I).

Suitable pharmaceutically acceptable salts of the object compounds (I) are conventional non-toxic salt and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, etc.), an inorganic acid salt (e.g. hydrochloride, hydrobromide, sulfate, phosphate, etc.), or a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable protected amino for $R^1$ and $R^{1a}$ may include an acylamino or an amino group substituted by a conventional protecting group such as ar(lower)alkyl which may have at least one suitable substituent(s), (e.g. benzyl, trityl, etc.) or the like.

Suitable acyl moiety in the terms "acylamino" and "acyloxy" for $R^{4a}$ may include carbamoyl, aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.); lower alkoxycarbonyl (e.g. methoxycarbonyl, ethoxycarbonyl, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.); arenesulfonyl (e.g. benzenesulfonyl, tosyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc.), and the like. The acyl moiety as stated above may have at least one suitable substituent(s) such as halogen (chlorine, bromine, fluorine and iodine) or the like.

Preferable examples of acylamino and acyloxy groups may include lower alkanoylamino, halogen substituted lower alkanoylamino; and lower alkanoyloxy; respectively.

Suitable saturated 4 to 8-membered heteromonocyclic group containing one sulfur atom for $R^2$ may include thietanyl, thiolanyl, thianyl, thiepanyl, thiocanyl and the like.

Suitable protected carboxy for $R^3$ may include an esterified carboxy and the like, and suitable examples of the ester moiety in said esterified carboxy may be the ones such as lower alkyl ester (e.g. methyl ester, ethyl ester, propyl ester, isopropyl ester, butyl ester, isobutyl ester, pentyl ester, hexyl ester, 1-cyclopropylethyl ester, etc.) which may have at least one suitable substituent(s), for example, lower alkanoyloxy(lower)alkyl ester (e.g. acetoxymethyl ester, propionyloxymethyl ester, butyryloxymethyl ester, valeryloxymethyl ester, pivaloyloxymethyl ester, 2-acetoxyethyl ester, 2-propionyloxyethyl ester, hexanoyloxymethyl ester, etc.), lower alkanesulfonyl(lower)alkyl ester (e.g. 2-mesylethyl ester, etc.) or mono(or di or tri)-halo(lower)alkyl ester (e.g. 2-iodoethyl ester, 2,2,2-trichloroethyl ester, etc.); lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-ditertiarybutylbenzyl ester, etc.); aryl ester which may have at least one suitable substituent(s) (e.g. phenyl ester, 4-chlorophenyl ester, tolyl ester, tertiarybutylphenyl ester, xylyl ester, mesityl ester, cumenyl ester, etc.), and the like.

Preferable example of the esterified carboxy as mentioned above may include lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl, etc.) and phenyl(lower)alkoxycarbonyl (e.g. benzyloxycarbonyl, diphenylmethoxycarbonyl, etc.).

Suitable "lower alkyl" for $R^4$ means straight or branched one and may include methyl, ethyl, propyl, isopropyl, butyl, isobutyl, t-butyl, pentyl, hexyl and the like.

The heterocyclic moiety in the terms "heterocyclicthio group which may have suitable substituent(s)" for $R^{4a}$ and $R^{4c}$ and "heterocyclicthiol which may have suitable substituent(s)" for $R^{4b}$ means saturated or unsaturated, monocyclic or polycyclic heterocyclic group containing at least one heteroatom such as an oxygen, sulfur, nitrogen atom and the like. And, especially preferable heterocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered heteromonocyclic group containing 1 to 4 nitrogen atom(s), for example, pyrrolidinyl, imidazolidinyl, piperidino, piperazinyl, etc.;

unsaturated condensed heterocyclic group containing 1 to 5 nitrogen atom(s), for example, indolyl, isoindolyl, indolizynyl, benzimidazolyl, quinolyl, isoquinolyl, indazolyl, benzotriazolyl, tetrazolopyridyl, tetrazolopyridazinyl, dihydrotriazolopyridazinyl, etc.;

unsaturated 3 to 8-membered heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.), etc.;

saturated 3 to 8-membered heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered heteromonocyclic group containing 1 to 2 sulfur atom(s) and 1 to 3 nitrogen atom(s), for example, thiazolidinyl, etc.;

unsaturated 3 to 8-membered heteromonocyclic group containing 1 to 2 sulfur atom(s), for example, thienyl, dihydrodithiinyl, dihydrodithiolyl, etc.; unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered heteromonocyclic group containing an oxygen atom, for example, furyl, etc.;

unsaturated 3 to 8-membered heteromonocyclic group containing an oxygen atom and 1 to 2 sulfur atom(s), for example, dihydrooxathiinyl, etc.;

unsaturated condensed heterocyclic group containing 1 to 2 sulfur atom(s); for example, benzothienyl, benzodithiinyl, etc.;

unsaturated condensed heterocyclic group containing an oxygen atom and 1 to 2 sulfur atom(s), for example, benzoxathiinyl, etc. and the like.

The heterocyclic moieties as mentioned above may have at least one substituent(s) such as lower alkyl (e.g. methyl, ethyl, propyl, isopropyl, butyl, isobutyl, tert-butyl, pentyl, neopentyl, tert-pentyl, hexyl, etc.);

lower alkenyl (e.g. vinyl, 1-propenyl, allyl, 1-methylallyl, 1 or 2 or 3-butenyl, 1 or 2 or 4-pentenyl, 1 or 2 or 3 or 4 or 5-hexenyl, etc.);

lower alkynyl (e.g. ethynyl, 1-propynyl, 2-propynyl, 1-methyl-2-propynyl, 1 or 2 or 3-butynyl, 1 or 2 or 3 or 4-pentynyl, 1 or 2 or 3 or 4 or 5-hexynyl, etc.); or the like.

Preferable example of heterocyclic moieties having suitable substituent(s) may include tetrazolyl having (lower)alkyl (e.g. methyltetrazolyl, ethyltetrazolyl, propyltetrazolyl, etc.), tetrazolyl having lower alkenyl [e.g. vinyltetrazolyl, (1-propenyl)tetrazolyl, allyltetrazolyl, (1-methylallyl)-tetrazolyl, (1 or 2 or 3-butenyl)tetrazolyl, etc.] tetrazolyl having lower alkynyl [e.g. ethynyltetrazolyl (1-propynyl)tetrazolyl, (2-propynyl)tetrazolyl, (1-methyl-2-propynyl)tetrazolyl, (1 or 2 or 3-butynyl)-tetrazolyl, etc.], and the like.

Suitable substituent(s) on pyridinio or pyridine in the terms "pyridinio which may have suitable substituent(s)" for $R^{4a}$ and $R^{4c}$ and "pyridine which may have suitable substituent(s)" for $R^{4b}$ may include carbamoyl and the like.

Suitable example of Y may include an acid residue such as azido, halogen (e.g. chlorine, bromine, fluorine, iodine), acyloxy as aforementioned, or the like.

Suitable hydroxy reactive derivative for X may include an acid residue such as halogen (e.g. chlorine, bromine, fluorine or iodine) or the like.

Suitable amino having a protective group for $R^5$ may include phthalimido, succinimido, ethoxycarbonylamino and the like, and preferably phthalimido.

Suitable lower alkanoyl in the term "lower alkanoylamino" for $R^{1b}$ may include formyl, acetyl, propionyl, butyryl, isobytyryl, valeryl, pivaloyl and the like.

Suitable "trihalo(lower)alkanoyl" in the term "trihalo(lower)alkanoylamino" for $R^{1c}$ may include trifluoroacetyl, trichloroacetyl, trifluoropropionyl, trifluorobutyryl and the like.

The preferable examples of the object compound (I) are exemplified as follows.

Preferable example of $R^1$ is amino, lower alkanoylamino or halogen substituted lower alkanoylamino;

$R^2$ is thietanyl;

$R^3$ is carboxy;

$R^4$ is hydrogen lower alkyl or a group of the formula: —$CH_2$—$R^{4a}$ [wherein preferable example of $R^{4a}$ is lower alkanoyloxy, thiadiazolylthio, tetrazolylthio having a lower alkyl, tetrazolylthio having a lower alkenyl, tetrazolylthio having a lower alkynyl, pyridinio or pyridinio having carbamoyl].

The processes for preparing the object compounds of the present invention are explained in details in the following.

PROCESS 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide or the like; a derivative formed by reaction of the compound (II) with phosphorus trichloride or phosgene, and the like.

Suitable salt of the compounds (II) and (III) may include an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a metal salt (e.g., sodium salt, potassium salt, calcium salt, magnesium salt, etc.); ammonium salt; an organic amine salt (e.g., triethylamine salt, dicyclohexylamine salt, etc.), and the like.

Suitable reactive derivative at the carboxy group of the compound (III) may include an acid halide, an acid anhydride, an activated amide, an activated ester, an the like. The suitable example may be an acid chloride, an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g., cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester p-cresyl thioester, carboxymethyl thioester, pyranyl ester, pyridyl ester, piperidyl ester, 8-quinolyl thioester, etc.), or an ester with a N-hydroxy compound (e.g., N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride; phosphorus trichloride; thionyl chloride; oxalyl chloride; triphenylphosphine; 2-ethyl-7-hydroxybenzisoxazolium salt; 2-ethyl-5-(m-sulphophenyl)isoxazolium hydroxide intra-molecular salt; 1-(p-chlorobenzenesulfonyloxy)-6-chloro-1H-benzotriazole; so-called Vilsmeier reagent prepared by the reaction of dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)-alkylbenzylamine, or the like. The reaction temperature is not critical, and the reaction is usually carried out under cooling or at ambient temperature.

In the present reaction, a syn isomer of the object compound (I) can be obtained preferably by conducting the present reaction of the compound (II) with the corresponding syn isomer of the starting compound (III), for example, in the presence of a Vilsmeier reagent as mentioned above etc. and under around neutral condition.

PROCESS 2

The object compound (Ib) or a salt thereof can be prepared by subjecting the compound (Ia) or a salt thereof to elimination reaction of the amino protective group.

Suitable salt of the compound (Ia) can be referred to those exemplified for the compound (II).

The elimination reaction is carried out in accordance with a conventional method such as hydrolysis; reduction; a method treating the compound (Ia) wherein $R^{1a}$ is acylamino with iminohalogenating agent, iminoetherifying agent and then, if necessary, hydrolyzing the resultant; or the like. The hydrolysis may include a method using an acid or base or hydrazine and the like. These methods may be selected depending on the kind of the protective groups to be eliminated.

Among these methods, hydrolysis using an acid is one of the most common and preferable method for eliminating the protective groups such as substituted or unsubstituted alkoxycarbonyl, for example, tert-pentyloxycarbonyl, lower alkanoyl (e.g., formyl, acetyl, etc.), cycloalkoxycarbonyl, substituted or unsubstituted aralkoxycarbonyl, aralkyl (e.g., trityl), substituted phenylthio, substituted aralkylidene, substituted alkylidene, substituted cycloalkylidene or the like. Suitable acid includes an organic or inorganic acid such as formic acid, trifluoroacetic acid, benenesulfonic acid, p-toluenesulfonic acid, hydrochloric acid and the like, and the most suitable acid is an acid which can easily be removed from the reaction mixture by a conventional manner such as distillation under reduced pressure, for example, formic acid, trifluoroacetic acid, hydrochloric acid, etc.

The acids can be selected according to the kind of the protective group to be eliminated. When the elimination reaction is conducted with an acid, it can be carried out in the presence or absence of a solvent. Suitable solvent includes water, a conventional organic solvent or a mixture thereof.

The elimination reaction using trifluoroacetic acid may be carried out in the presence of anisole. The hydrolysis using hydrazine is commonly applied for eliminating a phthaloyl, succinyl type aminoprotective group.

The hydrolysis using a base is preferably applied for elimination of an acyl group. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-ene, 1,4-diazabicyclo[2,2,2]octane, 1,5-diazabicyclo[5,4,0]undecene-5 or the like. The hydrolysis using a base is often carried out in water or a hydrophilic organic solvent or a mixed solvent thereof.

The reductive elimination is generally applied for eliminating the protective group, for example, haloalkoxycarbonyl (e.g. trichloroethoxycarbonyl, etc.), substituted or unsubstituted aralkoxy carbonyl (e.g. benzyloxycarbonyl, etc.), 2-pyridiylmethoxycarbonyl, etc. Suitable reduction may include, for example, reduction with an alkali metal borohydride (e.g. sodium borohydride, etc.), reduction with a combination of a metal (e.g. tin, zinc, iron, etc.) or the said metal together with a metal salt compound (e.g. chromous chloride, chromous acetate, etc.) and an organic or inorganic acid (e.g. acetic acid, propionic acid, hydrochloric acid, etc.); and catalytic reduction. Suitable catalyst includes a conventional one, for example, Raney nickel, platinum oxide, palladium on charcoal and the like.

Among the protective groups, the acyl group can generally be eliminated by hydrolysis. Especially, halogen substituted-alkoxycarbonyl and 8-quinolyloxycarbonyl groups are usually eliminated by treating with a heavy metal such as copper, zinc, or the like.

Among the protective groups, the acyl group can also be eliminated by treating with an iminohalogenating agent (e.g. phosphorus oxychloride, etc.) and an iminoetherifying agent such as lower alkanol (e.g. methanol, ethanol, etc.), if necessary, followed by hydrolysis.

The reaction temperature is not critical and may suitably be selected in accordance with the kind of the protective group for the amino group and the elimination method as mentioned above, and the reaction is preferably carried out under a mild condition such as under cooling or at slightly elevated temperature.

PROCESS 3

The object compound (Id) or a salt thereof can be prepared by reacting a compound (Ic) or a salt thereof with a compound (IX) or its reactive derivative.

Suitable salts of the compound (Ic) are referred to the ones exemplified for the compound (I).

Suitable reactive derivative in the compound (IX) may include a metal salt such as an alkali metal salt (e.g. sodium salt, potassium salt, etc.), an alkaline earth metal salt (e.g., magnesium salt, etc.) or the like.

The reaction may be carried out in the presence of sodium iodide, sodium thiocyanate and the like.

The reaction is usually carried out in a solvent such as water, acetone, chloroform, nitrobenzene, methylene chloride, ethylene chloride, dimethylformamide, methanol, ethanol, ether, tetrahydrofuran or any other conventional solvents which do not adversely influence the reaction, preferably in ones having strong polarity, which may be used as a mixture with water.

When the compound (Ic) and/or the compound (IX) are used in free form in the reactions, the reaction is preferably carried out in the presence of a base, for example, an organic or an inorganic base such as alkali metal hydroxide, alkali metal carbonate, alkali metal bicarbonate, trialkylamine, pyridine or the like, and preferably carried out around neutral conditions. The reaction temperature is not critical and the reaction is usually carried out at ambient temperature or under warming.

Processes for the preparation of the starting compounds (III) are explained in detail as follows.

PREPARATION 1 (IV)+(V)→(VI): [PROCESS (A)]

The compound (VI) can be prepared by reacting a compound (IV) with a compound (V).

The reaction is preferably carried out in the presence of a base as exemplified in Process 1 in case that X is an acid residue and in the presence of a condensing agent, for example, one formed by triphenylphosphine and diethyl azodicarboxylate in case that X is hydroxy, respectively.

The reaction is usually carried out in a solvent such as acetonitrile, dimethylformamide, tetrahydrofuran or any other solvents which do not adversely influence the reaction. The reaction temperature is not critical and the reaction is usually carried out from cooling to heating around a boiling point of the solvent used.

PREPARATION 2 (VI)→(VII): [PROCESS (A)]

The compound (VII) or a salt thereof can be prepared by subjecting a compound (VI) to elimination reaction of the amino protective group.

This elimination reaction of the amino protective group of the compound (VI) can be carried out in a similar manner to that of aforementioned

PROCESS 2

Suitable solvents include water, ethanol, chloroform, diethyl ether and the like. The reaction temperature is not critical and the reaction is usually carried out under warming or heating.

PREPARATION 3: (VII)+(VIII)→(III): [PROCESS (A)]

The compound (III) or a salt thereof can be prepared by reacting a compound (VII) or a salt thereof with a compound (VIII) or a salt thereof Suitable salts of the compound (VII) include an inorganic acid salt (e.g. hydrochloride, hydrobromide, sulfate, etc.), an organic acid salt (e.g. acetate, p-toluenesulfonate, etc.) and the like.

Suitable salts of the compound [VIII] are referred to the ones as exemplified for the compound [I].

The reaction is usually carried out in a conventional solvent such as water, alcohol (e.g. methanol, ethanol, etc.), a mixture thereof or any other ones which do not adversely influence the reaction.

When the compound (VII) is used in its salt form, the reaction is preferably carried out in the presence of an organic or an inorganic base as exemplified before.

The reaction temperature is not critical, and the reaction is usually carried out from cooling to heating.

In the present reaction, a syn isomer of the compound (III) can be obtained preferably by conducting the present reaction under around neutral conditions.

PREPARATION 4: (IIIa)→(IIIb) [PROCESS B]

(a) The compound (IIIb) or a salt thereof can be prepared by subjecting the compound (IIIa) or a salt thereof to the acyl exchange reaction.

The present acyl exchange reaction can be carried out by reacting the compound (IIIa) or a salt thereof with an acylating agent. Suitable acylating agent may include $R^6$—OH (IX) (Wherein $R^6$ is trihalo(lower)alkanoyl or its reactive derivatives or a salt thereof.

The present acyl exchange reaction can be carried out in a similar manner to that of aforementioned Process 1.

The present invention includes, within its scope, the cases that protected amino and/or protected carboxy group(s) are transformed into the corresponding free amino and/or carboxy group(s) according to the reaction conditions and kinds of the protective groups in the course of the aforementioned reactions and/or in post-treatment of the reactions in Processes 1 to 3 and A to B.

In the aforementioned reactions and/or the post-treating of the reactions in Processes 1 to 3 and A to B of the present invention, the aforementioned geometrical isomer and/or tautomeric isomer may occasionally be transformed into the other geometrical isomer and/or tautomeric isomer and such cases are to be also included in the scope of the present invention.

In case that the object compound (I) has a free carboxy group and/or a free amino group, it may be transformed into its pharmaceutically acceptable salt as aforementioned by a conventional method.

The object compound (I) of the present invention exhibits high antimicrobial activity and inhibits the growth of a number of microorganisms including pathogenic Gram-positive and Gram-negative bacteria.

For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives.

While the dosage of the compounds may vary from and also depend upon the age and condition of the patient, an average single dose of about 50 mg., 100 mg., 250 mg., and 500 mg. of the compounds according to the present invention has proved to be effective for treating of infectious diseases caused by a number of pathogenic bacteria. In general amounts, daily dose between 1 mg/body and about 1000 mg/body or even more may be administered.

Now, in order to show the utility of the object compounds (I), test data on anti-microbial activity of a representative compound of the present invention are shown below.

TEST METHOD

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of $\mu$g/ml after incubation at 37° C. for 20 hours.

TEST COMPOUND (1) 7-[2-(3-Thietanyloxyimino)-2-(2-aminothiazol-4-yl)acetamido]-3-(1-pyridiniomethyl)-3-cephem-4-carboxylate (syn isomer).

(2) 7-[2-(3-Thietanyloxyimino)-2-(2-aminothiazol-4-yl)acetamido]-3-(1-allyl-1H-tetrazol-5-yl)-thiomethyl-3-cephem-4-carboxylic acid (syn isomer).

TEST RESULT

| Test Microorganism | M.I.C. ($\mu$g/ml) | |
| --- | --- | --- |
| | Compound (I) | Compound (2) |
| *Staphylococcus aureus* 209P JC-1 | 0.390 | 0.780 |
| *Bacillus subtilis* ATCC 6633 | 0.200 | 1.560 |
| *Escherichia coli* 31 | 0.025 | 0.050 |
| *Klebsiella pneumoniae* 20 | 0.390 | 0.200 |

The following Preparations and Examples are given for the purpose of illustrating the present invention.

PREPARATION 1

Diethyl azodicarboxylate (4.3 g) was added all at once to a stirred mixture of 3-thietanol (2.0 g), N-hydroxyphthalimide (3.6 g) and triphenylphosphine (5.8 g) in dry tetrahydrofuran (100 ml) at room temperature. The temperature of the reaction mixture was raised to 40° C. The mixture became clear solution and was stirred for 12 hours at room temperature. Tetrahydrofuran was evaporated in vacuo and the residue was dissolved in ethyl acetate (50 ml). The insoluble substance was filtered off. The filtrate was washed three times with a saturated aqueous solution of sodium bicarbonate (50 ml) and with a saturated aqueous solution of sodium chloride (50 ml), dried over magnesium sulfate and evaporated. The residue was dissolved in methylene chloride (50 ml), subjected to column chromatography on silica gel and eluted with methylene chloride. The fractions containing the object compound were collected and evaporated in vacuo to give N-(3-thietanyloxy)phthalimide (2.0 g).

IR (Nujol): 1780, 1720, 1600, 1530 cm$^{-1}$

NMR (CDCl$_3$, $\delta$): 7.75 (4H, s), 5.2 (1H, m), 3.72, (2H, m), 3.22 (2H, m).

PREPARATION 2

Hydrazine hydrate (4.9 g) was added to a stirred suspension of N-(3-thietanyloxy)phthalimide (15.5 g) in ethanol (150 ml) at 60° C. and stirred for 1.5 hours at the same temperature. 4% Aqueous hydrochloric acid (170 ml) was added to the reaction mixture and insoluble substance was filtered off. The filtrate was concentrated to half of its original volume and the insoluble substance was filtered off again. To the filtrate containing N-(3-thietanyloxy)amine was added ethanol (100 ml) and the solution was adjusted to pH 7.0 with 4N aqueous solution of sodium hydroxide. After addition of 2-(2-formamidothiazol-4-yl)glyoxylic acid (10.1 g) to the solution, the suspension was adjusted to pH 4.5 with 10% hydrochloric acid and stirred for 2 hours at pH 4.0 to 4.5. After the reaction mixture was adjusted to pH 7.5 with a saturated aqueous solution of sodium bicarbonate, ethanol was evaporated and the aqueous solution was washed with ethyl acetate (100 ml). The aqueous layer was adjusted to pH 2.0 with 10% aqueous hydrochloric acid and extracted with ethyl acetate (100 ml). The ethyl acetate layer was washed with a saturated aqueous solution of sodium chloride (100 ml), dried over magnesium sulfate and evaporated. Recrystallization from ethyl acetate gave 2-(3-thietanyloxyimino)-2-(2-formamidothiazol-4-yl)acetic acid (syn isomer) (7.5 g).

IR (Nujol): 3200, 1730, 1710, 1600, 1550 cm$^{-1}$.

NMR (DMSO-d$_6$, $\delta$): 12.7 (1H, broads), 8.53, (1H, s), 7.6 (1H, s), 5.35 (1H, m), 3.42 (4H, m).

PREPARATION 3

Trifluoroacetic anhydride (26 g) was added to a stirred suspension of 2-(3-thietanyloxyimino)-2-(2-formamidothiazol-4-yl)acetic acid (syn isomer) (12 g) in tetrahydrofuran (120 ml) at −15° C. to −10° C. Triethylamine (8.5 g) was added to the reaction mixture at −10° to 3° C. and stirred for 1 hour at 3° to 5° C. The reaction mixture was poured to a mixture of ethyl acetate and a saturated aqueous solution of sodium bicarbonate. The separated aqueous layer was adjusted to pH 2.0 with 10% aqueous hydrochloric acid and extracted with ethyl acetate. The ethyl acetate layer was washed with a saturated aqueous solution of sodium chloride, dried over magnesium sulfate and evaporated. The residue was washed with ethyl acetate and filtered to give 2-(3-thietanyloxyimino)-2-[2-(2,2,2-trifluoroacetamido)-thiazol-4-yl]acetic acid (syn isomer) (12.3 g).

IR (Nujol): 3200, 1720, 1600, 1580 cm$^{-1}$.

NMR (DMSO-d$_6$, δ): 3.1–3.83 (4H, m), 5.37 (1H, t-t, J=8 and 8 Hz), 7.73 (1H, s).

PREPARATION 4

(1) A mixture of thiosemicarbazide (300 g), benzylchloride (416.7 g) in ethanol (1.5 l) was refluxed with stirring for an hour. The reaction mixture was cooled and evaporated under reduced pressure to give a crude oily product of 3-benzylisothiosemicarbazide hydrochloride.

Thus obtained crude product was used in the next step reaction without isolation.

(2) To a solution of the crude product of 3-benzylisothiosemicarbazide hydrochloride from 1) above in water (5 l) were added conc. hydrochloric acid (0.29 l) and benzene (2 l). The resulting mixture was cooled to 5° to 6° C. and thereto was dropwise added a solution of sodium nitrite (249 g) in water (1 l) over a period of an hour keeping the temperature below 15° C. The resulting mixture was stirred for 1.5 to 2 hours at about 10° C. The precipitates were collected by filtration, washed successively with benzene (1 l) and n-hexane (1 l) and then dried to give 5-benzylthio-1H-tetrazole (412.8 g), mp 98° to 100° C.

PREPARATION 5

A solution of 5-benzylthio-1H-tetrazole (278 g) in pyridine (2.7 l) was stirred at 60° to 70° C. and thereto was added sodium metal (100 g) over a period of 40 to 60 minutes. The resulting mixture was refluxed with stirring for 2.5 hours and then thereto was added methanol (200 ml). The mixture was stirred for 10 to 20 minutes. The reaction mixture was evaporated and the residue was dissolved in a mixture of water (0.8 l) and ethyl acetate (1 l). The solution was treated with activated charcoal (20 g) and the aqueous layer was separated and saturated with sodium chloride. The solution was adjusted to pH 2 with conc. hydrochloric acid and extracted with ethyl acetate (250 to 300 ml×7 to 10). The extract was dried over magnesium sulfate and then evaporated to give crystals of 1H-tetrazole-5-thiol (95.0 g), mp 178° to 180° C. (dec.).

PREPARATION 6

To a mixture of 1H-tetrazole-5-thiol (27.5 g) and triethylamine (59.9 g) in tetrahydrofuran (550 ml) was added benzhydryl bromide (66.6 g) and then the mixture was refluxed with stirring for 6.5 hours. After the addition of water and ethyl acetate to the reaction mixture, the pH was adjusted to 9.0 with 2N aqueous solution of sodium hydroxide. The aqueous layer was separated and washed with ethyl acetate. After the addition of ethyl acetate to the washed aqueous layer, the mixture was adjusted to pH 2.0 with 10% hydrochloric acid. The ethyl acetate layer was separated, washed with a saturated aqueous solution of sodium chloride, dried over magnesium sulfate and then evaporated. The residue was pulverized in a mixture of isopropyl ether and n-hexane, collected by filtration, washed with a mixture of isopropyl ether and n-hexane and then dried to give 5-benzhydrylthio-1H-tetrazole (29.62 g), mp 132° to 134° C.

N.M.R. (DMSO-d$_6$, δ): 6.32 (1H, s), 7.21–7.73 (10H, m).

PREPARATION 7

To a solution of 5-benzhydrylthio-1H-tetrazole (29 g) in tetrahydrofuran (145 ml) were added triethylamine (12.0 g) and 2-propynyl bromide (19.3 g) at room temperature. The resulting mixture was stirred for 2.5 hours at 40° to 45° C. The reaction mixture was filtered and the filtrate was evaporated. The residue was shaken with a mixture of ethyl acetate and water. The ethyl acetate layer was separated, washed with a saturated aqueous solution of sodium chloride, dried over magnesium sulfate and then evaporated. The residual oil (27.7 g) was subjected to column chromatography on silica gel, and eluted with a mixture of n-hexane, chloroform and ethyl acetate (5.5:4.5:0.5), to give 5-benzhydrylthio-2-(2-propynyl)-2H-tetrazole (14.2 g), mp 85° to 86° C.

I.R. (Nujol): 3260, 2150 cm$^{-1}$.

N.M.R. (DMSO-d$_6$, δ): 3.66 (1H, t, J=2.5 Hz), 5.61 (2H, d, J=2.5 Hz), 6.20 (1H, s), 7.17–7.66 (10H, m).

The continued elution gave 5-benzhydrylthio-1-(2-propynyl)-1H-tetrazole (8.97 g), mp 92° C.

I.R. (Nujol): 3300, 2150 cm$^{-1}$.

N.M.R. (DMSO-d$_6$, δ): 3.66 (1H, t, J=2.5 Hz), 5.34 (2H, d, J=2.5 Hz), 6.23 (1H, s), 7.20–7.66 (10H, m).

PREPARATION 8

A mixture of 5-benzhydrylthio-1-(2-propynyl)-1H-tetrazole (0.35 g), anisole (0.6 g) and trifluoroacetic acid (3.4 ml) was stirred for 30 minutes at 20° C. and then allowed to stand for 45 minutes. The reaction mixture was filtered and the filter cake was washed with isopropyl ether. The filtrate and the washing were combined and evaporated under reduced pressure. After the addition of the residue to a saturated aqueous solution of sodium bicarbonate precooled to 10° C., the resulting mixture was adjusted to pH 8.5 with 2N aqueous solution of sodium hydroxide and washed with ethyl acetate. The washed aqueous layer was adjusted to pH 2.5 with 10% hydrochloric acid under ice-cooling and then extracted with ethyl acetate. The extract was washed with a saturated aqueous solution of sodium chloride, dried over magnesium sulfate and evaporated to give 1-(2-propynyl)-1H-tetrazole-5-thiol (95 mg), which is decomposed from 60° to 71° C.

I.R. (Nujol): 3240, 2125 cm$^{-1}$.

N.M.R. (DMSO-d$_6$, δ): 3.47 (1H, t, J=2 Hz), 5.08 (2H, d, J=2 Hz).

PREPARATION 9

The following compounds were prepared according to the similar manner to that of Preparation 5.

(1) 1-(2-Propynyl)-1H-tetrazole-5-thiol

I.R. (Nujol): 3240, 2125 cm$^{-1}$.

PREPARATION 10

(1) A mixture of benzhydrylbromide (298.3 g) and thiosemicarbazide (100 g) in dry ethanol (1 l) was refluxed for 3 hours, and the ethanol was evaporated off under reduced pressure to give a crude oily product of 3-benzhydrylisothiosemicarbazide hydrobromide.

Thus obtained crude product was used in the next step reaction without isolation.

(2) To a mixture of the crude product of 3-benzhydrylisothiosemicarbazide hydrobromide from (1) above, water (2.3 l), conc. hydrochloric acid (126 g) and toluene (900 ml) was dropwise added a solution of sodium nitrite (83.5 g) in water (200 ml) and the resulting mixture was stirred for 1.5 hours at 10° to 15° C. The reaction mixture was extracted with ethyl acetate. The organic layer was added to water (1 l) and adjusted to pH 9.5 with 4N aqueous solution of sodium hydroxide. The separated aqueous layer was then adjusted to pH 2.5 with 10% hydrochloric acid and extracted with ethyl acetate. The ethyl acetate layer was washed with water, dried and evaporated to give a residue, which was washed with a mixture of n-hexane and isopropyl ether (2:1) and air-dried to give 5-benzhydrylthio-1H-tetrazole (127.22 g), mp. 132° to 134° C.

NMR (DMSO-$d_6$, $\delta$): 6.32 (1H, s), 7.21–7.73, (10H, m).

PREPARATION 11

To a suspension of 7-aminocephalosporanic acid (0.35 g) and 1-(2-propynyl)-1H-tetrazole-5-thiol (0.20 g) in acetonitril (1.8 ml) was added boron trifluoride etherate (0.55 g) at room temperature and the resulting mixture was stirred for 1.5 hours at 47° C. To the reaction mixture was added water (1.8 ml) and the mixture was adjusted to pH 3.5 with conc. aqueous ammonia under ice-cooling. The precipitates were collected by filtration, washed successively with water and acetone and then dried to give 7-amino-3-[1-(2-propynyl)-1H-tetrazole-5-yl]thiomethyl-3-cephem-4-carboxylic acid (0.36 g).

I.R. (Nujol): 3250, 3160, 2130 cm$^{-1}$.

N.M.R. (DMSO-$d_6$, $\delta$): 3.67 (3H, m), 4.38 (2H, q, J=14.0 Hz), 4.81 (1H, d, J=5.0 Hz), 4.98, (1H, d, J=5.0 Hz), 5.31 (2H, d, J=2.0 Hz).

EXAMPLE 1

Vilsmeir reagent was prepared from N,N-dimethylformamide (0.52 g) and phosphorus oxychloride (1.1 g) in a usual manner. 2-(3-Thietanyloxyimino)-2-(2-formamidothiazol-4-yl)acetic acid (syn isomer) (1.5 g) was added to the stirred suspension of Vilsmeir reagent in tetrahydrofuran (15 ml) under ice-cooling and the mixture was stirred for 30 minutes at below 5° C. The mixture became clear solution [Solution A]. A mixture of trimethylsilylacetamide (7.2 g) and 1-[(7-amino-4-carboxy-3-cephem-3-yl)methyl]pyridinium chloride hydrochloride (2.0 g) in tetrahydrofuran (40 ml) was stirred at 45° C. for 30 minutes. To the mixture was added the above Solution A all at once at −30° C., and the resulting solution was stirred at −15° C. for 30 minutes. Water (50 ml) and ethyl acetate (50 ml) were added to the reaction mixture at −10° C. The organic layer was separated and the aqueous layer was extracted twice with a mixture of ethyl acetate (50 ml) and tetrahydrofuran (50 ml). The combined organic layers were dried over magnesium sulfate and evaporated in vacuo. The residue was pulverized with diisopropyl ether to give 7-[2-(3-thietanyloxyimino)-2-(2-formamidothiazol-4-yl)acetamido]-3-(1-pyridiniomethyl)-3-cephem-4-carboxylate (syn isomer) (1.2 g).

IR (Nujol): 3100–3400, 1770, 1660, 1610, 1540 cm$^{-1}$.

NMR (DMSO-$d_6$, $\delta$): 9.77 (1H, d, J=8 Hz), 9.3 (2H, m), 8.7 (1H, m), 8.57 (1H, s), 8.25 (2H, m), 7.48 (1H, s), 5.92 (1H, dd, J=5 and 8 Hz), 5.28 (1H, d, J=5 Hz), 5.0–5.83 (3H, m), 2.95–3.9 (6H, m).

EXAMPLE 2

Vilsmeir reagent was prepared from phosphorus oxychloride (1.2 g) and dimethylformamide (0.56 g) in a usual manner. 2-(3-Thietanyloxyimino)-2-[2-(2,2,2-trifluoroacetamido)thiazol-4-yl]acetic acid (syn isomer) (2.5 g) was added to the stirred suspension of Vilsmeir reagent in ethyl acetate (25 ml) under ice cooling, and stirred for 30 minutes at the same temperature to produce an activated acid solution. On the other hand, 7-aminocephalosporanic acid (2.1 g) was dissolved in a solution of trimethylsilylacetamide (6.1 g) in ethyl acetate (20 ml). To the solution was added the above activated acid solution at −20° C. and the mixture was stirred for 1 hour at −20° to −5° C. Water and ethyl acetate were added to the reaction mixture and the separated ethyl acetate layer was washed with a saturated aqueous solution of sodium chloride and dried over magnesium sulfate. The solvent was evaporated to give 7-[2-(3-thietanyloxyimino)-2-{2-(2,2,2-trifluoroacetamido)thiazol-4-yl}acetamido]-cephalosporanic acid (syn isomer) (4.0 g).

IR (Nujol): 3250, 1790, 1720, 1680, 1658, 1580, 1525 cm$^{-1}$.

NMR (DMSO-$d_6$, $\delta$): 2.05 (3H, s), 3.13–3.90 (4H, m), 3.67 (2H, m), 4.87 (2H, q, J=12 Hz), 5.23 (1H, d, J=5 Hz), 5.33 (1H, t-t, J=8 and 8 Hz), 5.88 (1H, dd, J=5,8 Hz), 7.60 (1H, s), 9.80 (1H, d, J=8 Hz).

EXAMPLE 3

The following compounds were prepared according to similar manners to those of Examples 1 and 2.

(1) 7-[2-(3-Thietanyloxyimino)-2-(2-aminothiazol-4-yl)acetamido]-3-(1-pyridiniomethyl)-3-cephem-4-carboxylate (syn isomer).

IR (Nujol): 3100–3400, 1770, 1660, 1620, 1530 cm$^{-1}$.

(2) 7-[2-(3-Thietanyloxyimino)-2-(2-aminothiazol-4-yl)acetamido]cephalosporanic acid (syn isomer).

IR (Nujol): 3250, 1760, 1730 (shoulder), 1650, 1540 cm$^{-1}$.

(3) 7-[2-(3-Thietanyloxyimino)-2-{2-(2,2,2-trifluoroacetamido)thiazol-4-yl}acetamido]-3-cephem-4-carboxylic acid (syn isomer).

IR (Nujol): 3290, 1790, 1722, 1682, 1650, 1620, 1585, 1520 cm$^{-1}$.

NMR (DMSO-$d_6$, $\delta$): 3.1–3.9 (4H, m), 3.70, (2H, broad s), 5.20 (1H, d, J=5 Hz), 5.37 (1H, tt, J=8 and 8 Hz), 5.93 (1H, dd, J=5 and 8 Hz), 6.53 (1H, m), 7.60 (1H, s), 9.83 (1H, d, J=8 Hz).

(4) 7-[2-(3-Thietanyloxyimino)-2-(2-aminothiazol-4-yl)acetamido]-3-cephem-4-carboxylic acid (syn isomer).

IR (Nujol): 3400, 3250, 1770, 1650, 1620, 1600, 1530 cm$^{-1}$.

(5) 7-[2-(3-Thietanyloxyimino)-2-(2-formamidothiazol-4-yl)acetamido]-3-(1,3,4-thiadiazol-2-yl)thiomethyl-3-cephem-4-carboxylic acid (syn isomer).

IR (Nujol): 3100–3400, 1780, 1720, 1660, 1560 cm$^{-1}$.

NMR (DMSO-$d_6$, $\delta$): 3.75–3.1 (4H, m), 3.77 (2H, broad s), 4.47 (2H, q, J=14 Hz), 5.63–5.08 (1H, m), 5.23 (1H, d, J=5 Hz), 5.88 (1H, dd, J=5 and 8 Hz), 7.51 (1H, s), 8.6 (1H, s), 9.63 (1H, s), 9.8 (1H, d, J=8 Hz), 12.8 (1H, broad s).

(6) 7-[2-(3-Thietanyloxyimino)-2-(2-aminothiazol-4-yl)acetamido]-3-(1,3,4-thiadiazol-2-yl)thiomethyl-3-cephem-4-carboxylic acid hydrochloride (syn isomer).

IR (Nujol): 3100–3400, 1770, 1660, 1620, 1540 cm$^{-1}$.

(7) 7-[2-(3-Thietanyloxyimino)-2-(2-formamidothiazol-4-yl)acetamido]-3-[1-(2-propynyl)-1H-tetrazol-5-yl]thiomethyl-3-cephem-4-carboxylic acid (syn isomer).

IR (Nujol): 3220, 1780, 1675 cm$^{-1}$.

NMR (DMSO-$d_6$, $\delta$): 3.13–3.90 (7H, m), 4.43 (2H, ABq, J=14 Hz), 5.16–5.55 (4H, m), 5.89 (1H, dd, J=5 Hz and 8 Hz), 7.49 (1H, s), 8.53 (1H, s), 9.73 (1H, d, J=8 Hz).

(8) 7-[2-(3-Thietanyloxyimino)-2-(2-aminothiazol-4-yl)acetamido]-3-[1-(2-propynyl)-1H-tetrazol-5-yl]thiomethyl-3-cephem-4-carboxylic acid hydrochloride (syn isomer).

IR (Nujol): 3240, 2100, 1770, 1670, 1625 cm$^{-1}$ (9) 7-[2-(3-Thietanyloxyimino)-2-{2-(2,2,2-trifluoroacetamido)thiazol-4-yl}acetamido]-3-(1-methyl-1H-tetrazol-5-yl)thiomethyl-3-cephem-4-carboxylic acid (syn isomer).

IR (Nujol): 3180, 1770, 1720, 1670 cm$^{-1}$.

NMR (DMSO-d$_6$, δ): 3.06–3.90 (4H, m), 3.74 (2H, m), 3.96 (3H, s), 4.36 (2H, q, J=14.0 Hz), 5.20 (1H, d, J=4.0 Hz), 5.06–5.53 (1H, m), 5.86 (1H, dd, J=4.0 and 8.0 Hz), 7.60 (1H, s), 9.81 (1H, d, J=8.0 Hz).

(10) 7-[2-(3-Thietanyloxyimino)-2-(2-aminothiazol-4-yl)acetamido]-3-(1-methyl-1H-tetrazol-5-yl)-thiomethyl-3-cephem-4-carboxylic acid (syn isomer).

IR (Nujol): 3300, 1770, 1650 cm$^{-1}$

(11) 7-[2-(3-Thietanyloxyimino)-2-{2-(2,2,2-trifluoroacetamido)thiazol-4-yl}acetamido]-3-(1-allyl-1H-tetrazol-5-yl)thiomethyl-3-cephem-4-carboxylic acid (syn isomer).

IR (Nujol): 3160, 1770, 1710, 1660 cm$^{-1}$.

NMR (DMSO-d$_6$, δ): 3.07–3.97 (4H, m), 3.70 (2H, m), 4.40 (2H, q, J=14.0 Hz), 4.80–5.53 (6H, m), 5.67–6.43 (2H, m), 7.61 (1H, s), 9.81 (1H, d, J=8.0 Hz).

(12) 7-[2-(3-Thietanyloxyimino)-2-(2-aminothiazol-4-yl)acetamido]-3-(1-allyl-1H-tetrazol-5-yl)thiomethyl-3-cephem-4-carboxylic acid (syn isomer).

IR (Nujol): 3300, 1770, 1670, 1630 cm$^{-1}$.

(13) 7-[2-(2-Trifluoroacetamidothiazol-4-yl)-2-(3-thietanyloxyimino)acetamido]-3-methyl-3-cephem-4-carboxylic acid (syn isomer).

IR (Nujol): 3230, 1780, 1720, 1660 cm$^{-1}$.

NMR (DMSO-d$_6$, δ): 2.60 (3H, s), 3.14–3.81 (6H, m), 5.17 (1H, d, J=5.0 Hz), 5.34 (1H, t, J=8.0 Hz), 5.76 (1H, dd, J=5.0 and 8.0 Hz), 7.59 (1H, s), 9.74 (1H, d, J=8.0 Hz).

(14) 7-[2-(2-Aminothiazol-4-yl)-2-(3-thietanyloxyimino)-acetamido]-3-methyl-3-cephem-4-carboxylic acid (syn isomer).

IR (Nujol): 3250, 1760, 1655 cm$^{-1}$.

(15) 7-[2-(2-Aminothiazol-4-yl)-2-(3-thietanyloxyimino)-acetamido]-3-(3-carbamoyl-1-pyridiniomethyl)-3-cephem-4-carboxylate (syn isomer).

IR (Nujol): 3300, 3180, 1775, 1670, 1610 cm$^{-1}$.

EXAMPLE 4

A mixture of 7-[2-(3-thietanyloxyimino)-2-(2-formamidothiazol-4-yl)acetamido]-3-(1-pyridiniomethyl)-3-cephem-4-carboxylate (syn isomer) (1.1 g) and conc. hydrochloric acid (0.8 g) in methanol (80 ml) was stirred at room temperature for 3 hours. Methanol was evaporated in vacuo and the residue was pulverized with isopropyl ether. The solid was dissolved in water (50 ml) and the solution was adjusted to pH 2.0 with 10% hydrochloric acid. The insoluble substance was filtered off. The filtrate was subjected to column chromatography on macroporous non-ionic adsorption resin "Diaion HP-20" (Trademark: prepared by Mitsubishi Chemical Industries) and eluted with 10% aqueous solution of isopropyl alcohol. The fractions containing the object compound were concentrated and lyophilized to give 7-[2-(3-thietanyloxyimino)-2-(2-aminothiazol-4-yl)-acetamido]-3-(1-pyridiniomethyl)-3-cephem-4-carboxylate (syn isomer) (0.45 g).

IR(Nujol): 3100–3400, 1770, 1660, 1620, 1530 cm$^{-1}$.

NMR (D$_2$O, δ): 9.0 (2H, m), 8.37–8.82 (1H, m), 7.88–8.37 (2H, m), 7.05 (1H, s), 5.92, (1H, d, J=5 Hz), 5.08–5.78 (3H, m), 5.33, (1H, d, J=5 Hz), 3.05–4.0 (6H, m).

EXAMPLE 5

A mixture of 7-[2-(3-thietanyloxyimino)-2{2-(2,2,2-trifluoroacetamido)thiazol-4-yl}acetamido]-cephalosporanic acid (syn isomer) (3.9 g) and sodium acetate (8.7 g) in water (70 ml) and tetrahydrofuran (15 ml) was stirred for 21 hours at room temperature. The reaction mixture was adjusted to pH 2.0 with conc. hydrochloric acid and extracted with a mixture of ethyl acetate and tetrahydrofuran (7:3). The organic layer was washed with a saturated aqueous solution of sodium chloride and dried over magnesium sulfate and evaporated. The residue was washed with isopropyl ether and filtered to give 7-[2-(3-thietanyloxyimino)-2-(2-aminothiazol-4-yl)acetamido]-cephalosporanic acid (syn isomer) (2.4 g).

IR (Nujol): 3250, 1760, 1730 (shoulder), 1650, 1540 cm$^{-1}$.

NMR (DMSO-d$_6$, δ): 2.05 (3H, s), 3.07–3.83 (4H, m, 3.60 (2H, s), 4.87 (2H, q, J=13 Hz), 5.20 (1H, d, J=5 Hz), 5.28 (1H, tt, J=8 and 8 Hz), 5.82, (1H, dd, J=5 and 8 Hz), 6.82 (1H, s), 9.63, (1H, d, J=8 Hz).

EXAMPLE 6

The following compounds were prepared according to similar manners to those of Examples 4 and 5.

(1) 7-[2-(3-Thietanyloxyimino)-2-(2-aminothiazol-4-yl)acetamido]-3-cephem-4-carboxylic acid (syn isomer).

IR (Nujol): 3400, 3250, 1770, 1650, 1620, 1600, 1530 cm$^{-1}$.

NMR (DMSO-d$_6$, δ): 3.0–3.83 (4H, m), 3.60 (2H, broad s), 5.13 (1H, d, J=5 Hz), 5.28 (1H, tt, J=8 and 8 Hz), 5.85 (1H, dd, J=5 and 8 Hz), 6.50 (1H, m), 6.80 (1H, s), 9.63 (1H, d, J=8 Hz).

(2) 7-[2-(3-Thietanyloxyimino)-2-(2-aminothiazol-4-yl)acetamido]-3-(1,3,4-thiadiazol-2-yl)-thiomethyl-3-cephem-4-carboxylic acid hydrochloride (syn isomer).

IR (Nujol): 3100-3400, 1770, 1660, 1620, 1540 cm$^{-1}$.

NMR (DMSO-d$_6$, δ): 3.8–3.1 (4H, m), 3.78 (2H, broad s), 4.5 (2H, q, J=14 Hz), 5.63–5.1 (1H, m), 5.25 (1H, d, J=5 Hz), 5.85 (1H, dd, J=5, 8 Hz), 7.07 (1H, s), 9.68 (1H, s), 9.97 (1H, d, J=8 Hz).

(3) 7-[2-(3-Thietanyloxyimino)-2-(2-aminothiazol-4-yl)acetamido]-3-[1-(2-propynyl)-1H-tetrazol-5-yl]-thiomethyl-3-cephem-4-carboxylic acid hydrochloride (syn isomer).

IR (Nujol): 3240, 2100, 1770, 1670, 1625 cm$^{-1}$.

NMR (DMSO-d$_6$, δ): 3.10–3.90 (7H, m), 4.43, (2H, ABq, J=14 Hz), 5.07–5.55 (4H, m), 5.80 (1H, dd, J=5 Hz and 8 Hz), 7.07, (1H, s), 9.84 (1H, d, J=8 Hz).

(4) 7-[2-(3-Thietanyloxyimino)-2-(2-aminothiazol-4-yl)acetamido]-3-(1-methyl-1H-tetrazol-5-yl)-thiomethyl-3-cephem-4-carboxylic acid (syn isomer).

IR (Nujol): 3300, 1770, 1650 cm$^{-1}$.

NMR (DMSO-d$_6$, δ): 3.07–3.78 (6H, m), 3.92, (3H, s), 4.31 (2H, q, J=14.0 Hz), 5.00–5.43 (1H, m), 5.14 (1H, d, J=5 Hz), 5.76 (1H, dd, J=5.0 and 8.0 Hz), 6.75 (1H, s), 7.26 (2H, broad s), 9.58 (1H, d, J=8.0 Hz).

(5) 7-[2-(3-Thietanyloxyimino)-2-(2-aminothiazol-4-yl)acetamido]-3-(1-allyl-1H-tetrazol-5-yl)-thiomethyl-3-cephem-4-carboxylic acid (syn isomer).

IR (Nujol): 3300, 1770, 1670, 1630 cm$^{-1}$.

NMR (DMSO-d$_6$, δ): 3.11–3.78 (6H, m), 4.34 (2H, q, J=14.0 Hz), 4.79–5.47 (6H, m), 5.65–6.25 (1H, m), 5.77

(1H, dd, J=5.0 and 8.0 Hz), 6.74 (1H, s), 7.19 (2H, broad s), 9.55 (1H, d, J=8.0 Hz).

(6) 7-[2-(2-Aminothiazol-4-yl)-2-(3-thietanyloxyimino)-acetamido]-3-methyl-3-cephem-4-carboxylic acid (syn isomer).

IR (Nujol): 3250, 1760, 1655 cm$^{-1}$.

NMR (DMSO-d$_6$, δ): 2.20 (3H, s), 3.06–3.81 (6H, m), 5.12 (1H, d, J=5.0 Hz), 5.26 (1H, t, J=8.0 Hz), 5.71 (1H, dd, J=5.0 and 8.0 Hz), 6.78 (1H, s), 7.21 (2H, broad s), 9.59 (1H, d, J=8.0).

(7) 7-[2-(2-Aminothiazol-4-yl)-2-(3-thietanyloxyimino)-acetamido]-3-(3-carbamoyl-1-pyridiniomethyl)-3-cephem-4-carboxylate acid (syn isomer)

IR (Nujol): 3300, 3180, 1775, 1670, 1610 cm$^{-1}$.

EXAMPLE 7

Nicotinamide (2.85 g) and sodium iodide (9.8 g) were added to a stirred suspension of 7-[2-(2-aminothiazol-4-yl)-2-(3-thietanyloxyimino)acetamido]-cephalosporanic acid (syn isomer) (2.4 g) and sodium bicarbonate (0.4 g) in water (15 ml) at ambient temperature and the mixture was stirred for 50 minutes at 80° C. The resulting solution was cooled and washed with ethylacetate. The aqueous layer was adjusted to pH 1.0 with 10% hydrochloric acid and an insoluble material was filtered off. The filtrate was washed with ethyl acetate and adjusted pH 4.0 with a saturated aqueous solution of potassium carbonate. The solution was subjected to column chromatography on macroporus non-ionic adsoption resin "Diaion HP-20" and eluted with 10% aqueous solution of isopropyl alcohol. The fractions containing the object compound was concentrated and lyophilized to give 7-[2-(2-aminothiazol-4-yl)-2-(3-thietanyloxyimino)acetamido]-3-(3-carbamoyl-1-pyridiniomethyl)-3-cephem-4-carboxylate (syn isomer) (0.2 g).

| IR (Nujol) | NMR (DMSO-d$_6$, δ) |
| --- | --- |
| 3300 | 3.00–3.64 (6H, m) |
| 3180 | 5.09 (1H, d, J = 5.0 Hz) |
| 1775 | 5.19 (1H, t, J = 7.0 Hz) |
| 1670 | 5.64 (2H, m) |
| 1610 cm$^{-1}$ | 5.70 (1H, d–d, J = 5.0 Hz 8.0 Hz) |
| | 6.74 (1H, s) |
| | 7.20 (2H, br-s) |
| | 7.94–8.38 (2H, m) |
| | 8.88 (1H, m) |
| | 9.52 (1H, d, J = 8.0 Hz) |
| | 9.64 (1H, m) |

EXAMPLE 8

The following compounds were prepared according to similar manners to those of Example 7.

(1) 7-[2-(3-thietanyloxyimino)-2-(2-formamidothiazol-4-yl)acetamido]-3-(1-pyridiniomethyl)-3-cephem-4-carboxylate (syn isomer) (1.2 g).

IR (Nujol): 3100–3400, 1770, 1660, 1610, 1540 cm$^{-1}$.

(2) 7-[2-(3-Thietanyloxyimino)-2-(2-aminothiazol-4-yl)acetamido]-3-(1-pyridiniomethyl)-3-cephem-4-carboxylate (syn isomer).

IR (Nujol): 3100–3400, 1770, 1660, 1620, 1530 cm$^{-1}$.

(3) 7-[2-(3-Thietanyloxyimino)-2-(2-formamidothiazol-4-yl)acetamido]-3-(1,3,4-thiadiazol-2-yl)thiomethyl-3-cephem-4-carboxylic acid (syn isomer).

IR (Nujol): 3100–3400, 1780, 1720, 1660, 1560 cm$^{-1}$.

(4) 7-[2-(3-Thietanyloxyimino)-2-(2-aminothiazol-4-yl)acetamido]-3-(1,3,4-thiadiazol-2-yl)thiomethyl-3-cephem-4-carboxylic acid hydrochloride (syn isomer).

IR (Nujol): 3100–3400, 1770, 1660, 1620, 1540 cm$^{-1}$.

(5) 7-[2-(3-Thietanyloxyimino)-2-(2-formamidothiazol-4-yl)acetamido]-3-[1-(2-propynyl)-1H-tetrazol-5-yl]thiomethyl-3-cephem-4-carboxylic acid (syn isomer).

IR (Nujol): 3220, 1780, 1675 cm$^{-1}$.

(6) 7-[2-(3-Thietanyloxyimino)-2-(2-aminothiazol-4-yl)acetamido]-3-[1-(2-propynyl)-1H-tetrazol-5-yl]thiomethyl-3-cephem-4-carboxylic acid hydrochloride (syn isomer).

IR (Nujol): 3240, 2100, 1770, 1670, 1625 cm$^{-1}$.

(7) 7-[2-(3-Thietanyloxyimino)-2-{2-(2,2,2-trifluoroacetamido)thiazol-4-yl}acetamido]-3-(1-methyl-1H-tetrazol-5-yl)thiomethyl-3-cephem-4-carboxylic acid (syn isomer).

IR (Nujol): 3180, 1770, 1720, 1670 cm$^{-1}$.

(8) 7-[2-(3-Thietanyloxyimino)-2-(2-aminothiazol-4-yl)acetamido]-3-(1-methyl-1H-tetrazol-5-yl)-thiomethyl-3-cephem-4-carboxylic acid (syn isomer).

IR (Nujol): 3300, 1770, 1650 cm$^{-1}$.

(9) 7-[2-(3-Thietanyloxyimino)-2-{2-(2,2,2-trifluoroacetamido)thiazol-4-yl}acetamido]-3-(1-allyl-1H-tetrazol-5-yl)thiomethyl-3-cephem-4-carboxylic acid (syn isomer).

IR (Nujol): 3160, 1770, 1710, 1660 cm$^{-1}$.

(10) 7-[2-(3-Thietanyloxyimino)-2-(2-aminothiazol-4-yl)acetamido]-3-(1-allyl-1H-tetrazol-5-yl)-thiomethyl-3-cephem-4-carboxylic acid (syn isomer).

IR (Nujol): 3300, 1770, 1670, 1630 cm$^{-1}$.

What we claim is:

1. A compound of the formula $$R^1 \underset{S}{\overset{N}{\diagdown\!\!\!\diagup}} \underset{\underset{O-R^2}{\overset{\|}{N}}}{C} - COOH$$

wherein $R^1$ is amino or a protected amino group; and $R^2$ is a saturated 4 to 8-membered heteromonocyclic group containing one sulfur atom selected from the group consisting of thietanyl, thiolanyl, thianyl, thiepanyl and thiocanyl, and a salt thereof.

2. The compound of claim 1, wherein $R^2$ is thietanyl.
3. The compound of claim 1, wherein $R^2$ is thiolanyl.
4. The compound of claim 1, wherein $R^2$ is thianyl.
5. The compound of claim 1, wherein $R^2$ is thiepanyl.
6. The compound of claim 1, wherein $R^2$ is thiocanyl.

* * * * *